United States Patent
Moriarty et al.

(10) Patent No.: US 10,492,842 B2
(45) Date of Patent: Dec. 3, 2019

(54) MONITORING AND CONTROLLING INTERNALLY ADMINISTERED CRYOTHERAPY

(71) Applicant: Medtronic Ardian Luxembourg S.a.r.l., Luxembourg (LU)

(72) Inventors: Micheal Moriarty, Galway (IE); Brian Kelly, Galway (IE)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 1341 days.

(21) Appl. No.: 14/200,944

(22) Filed: Mar. 7, 2014

(65) Prior Publication Data

US 2015/0250524 A1  Sep. 10, 2015

(51) Int. Cl.
   *A61B 18/02* (2006.01)
   *A61B 18/00* (2006.01)
   *A61B 90/00* (2016.01)

(52) U.S. Cl.
   CPC ...... *A61B 18/02* (2013.01); *A61B 2018/0022* (2013.01); *A61B 2018/00404* (2013.01); *A61B 2018/00434* (2013.01); *A61B 2018/00511* (2013.01); *A61B 2018/00672* (2013.01); *A61B 2018/00714* (2013.01);
   (Continued)

(58) Field of Classification Search
   CPC ............................................. A61B 2018/0022
   See application file for complete search history.

(56) References Cited

U.S. PATENT DOCUMENTS

| 3,125,096 A | 3/1964 | Antiles et al. |
| 3,298,371 A | 1/1967 | Lee |

(Continued)

FOREIGN PATENT DOCUMENTS

| DE | 4406451 | 9/1995 |
| DE | 102005041601 | 4/2007 |

(Continued)

OTHER PUBLICATIONS

Beale et al., "Minimally Invasive Treatment for Varicose Veins: A Review of Endovenous Laser Treatment and Radiofrequency Ablation". Lower Extremity Wounds 3(4), 2004, 10 pages.

(Continued)

*Primary Examiner* — Luther Behringer
(74) *Attorney, Agent, or Firm* — Snell & Wilmer L.L.P.

(57) ABSTRACT

A method of using a cryotherapeutic system in accordance with a particular embodiment includes advancing an elongate shaft of a catheter toward a treatment location within a body lumen of a human patient and directing a flow of refrigerant toward a cryotherapeutic element at a distal end portion of the shaft. The directed refrigerant is expanded to cause cooling within a balloon of the cryotherapeutic element. The pressure within the balloon is monitored and its rate of change calculated. The rate of change is then processed using different feedback loops during different monitoring windows of a treatment cycle. The individual feedback loops include an upper and a lower threshold and are configured to cause the flow of refrigerant to the cryotherapeutic element to stop if the rate of change falls outside a range between the upper and the lower threshold.

15 Claims, 5 Drawing Sheets

(52) U.S. Cl.
CPC ............... *A61B 2018/00791* (2013.01); *A61B 2018/0212* (2013.01); *A61B 2018/0262* (2013.01); *A61B 2090/064* (2016.02)

(56) References Cited

U.S. PATENT DOCUMENTS

| | | | |
|---|---|---|---|
| 3,901,241 A | 8/1975 | Allen, Jr. | |
| 3,924,628 A | 12/1975 | Droegemueller et al. | |
| 4,275,734 A | 6/1981 | Mitchiner | |
| 4,483,341 A | 11/1984 | Witteles | |
| 4,602,624 A | 7/1986 | Naples et al. | |
| 4,649,936 A | 3/1987 | Ungar et al. | |
| 4,709,698 A | 12/1987 | Johnston et al. | |
| 4,764,504 A | 8/1988 | Johnson et al. | |
| 4,890,623 A | 1/1990 | Cook et al. | |
| 4,976,711 A | 12/1990 | Parins et al. | |
| 5,108,390 A | 4/1992 | Potocky et al. | |
| 5,190,539 A | 3/1993 | Fletcher et al. | |
| 5,300,068 A | 4/1994 | Rosar et al. | |
| 5,308,323 A | 5/1994 | Sodawa et al. | |
| 5,334,181 A | 8/1994 | Rubinsky et al. | |
| 5,342,301 A | 8/1994 | Saab | |
| 5,358,514 A | 10/1994 | Schulman et al. | |
| 5,368,591 A | 11/1994 | Lennox et al. | |
| 5,383,856 A | 1/1995 | Bersin | |
| 5,417,355 A | 5/1995 | Broussalian et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,624,392 A | 4/1997 | Saab | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,758,505 A | 6/1998 | Dobak, III et al. | |
| 5,772,590 A | 6/1998 | Webster, Jr. | |
| 5,807,391 A | 9/1998 | Wijkamp | |
| 5,837,003 A | 11/1998 | Ginsburg | |
| 5,860,970 A | 1/1999 | Goddard et al. | |
| 5,860,974 A | 1/1999 | Abele et al. | |
| 5,865,787 A | 2/1999 | Shapland et al. | |
| 5,868,735 A | 2/1999 | Lafontaine | |
| 5,893,885 A | 4/1999 | Webster et al. | |
| 5,902,299 A | 5/1999 | Jayaraman | |
| 5,944,710 A | 8/1999 | Dev et al. | |
| 5,954,719 A | 9/1999 | Chen et al. | |
| 5,971,979 A | 10/1999 | Joye et al. | |
| 5,983,141 A | 11/1999 | Sluijter et al. | |
| 6,004,269 A | 12/1999 | Crowley et al. | |
| 6,009,877 A | 1/2000 | Edwards | |
| 6,012,457 A | 1/2000 | Lesh | |
| 6,024,740 A | 2/2000 | Lesh et al. | |
| 6,024,752 A | 2/2000 | Horn et al. | |
| 6,032,675 A | 3/2000 | Rubinsky | |
| 6,036,687 A | 3/2000 | Laufer et al. | |
| 6,056,744 A | 5/2000 | Edwards | |
| 6,066,134 A | 5/2000 | Eggers et al. | |
| 6,091,995 A | 7/2000 | Ingle et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,142,991 A | 11/2000 | Schatzberger | |
| 6,142,993 A | 11/2000 | Whayne et al. | |
| 6,149,620 A | 11/2000 | Baker et al. | |
| 6,161,048 A | 12/2000 | Sluijter et al. | |
| 6,161,049 A | 12/2000 | Rudie et al. | |
| 6,161,543 A | 12/2000 | Cox et al. | |
| 6,164,283 A | 12/2000 | Lesh | |
| 6,190,356 B1 | 2/2001 | Bersin | |
| 6,219,577 B1 | 4/2001 | Brown, III et al. | |
| 6,224,592 B1 | 5/2001 | Eggers et al. | |
| 6,237,355 B1 | 5/2001 | Li | |
| 6,241,722 B1 | 6/2001 | Dobak et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,283,959 B1 | 9/2001 | Lalonde et al. | |
| 6,290,696 B1 | 9/2001 | Lafontaine | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,355,029 B1 | 3/2002 | Joye et al. | |
| 6,405,732 B1 | 6/2002 | Edwards et al. | |
| 6,413,255 B1 | 7/2002 | Stern | |
| 6,428,534 B1 | 8/2002 | Joye et al. | |
| 6,432,102 B2 | 8/2002 | Joye et al. | |
| 6,451,045 B1 | 9/2002 | Walker et al. | |
| 6,468,297 B1 | 10/2002 | Williams et al. | |
| 6,477,658 B1 * | 11/2002 | Pang ................ G01R 31/31725 713/501 |
| 6,488,679 B1 | 12/2002 | Swanson et al. | |
| 6,496,737 B2 | 12/2002 | Rudie et al. | |
| 6,497,703 B1 | 12/2002 | Korteling et al. | |
| 6,506,189 B1 | 1/2003 | Rittman, III et al. | |
| 6,514,226 B1 | 2/2003 | Levin et al. | |
| 6,514,245 B1 | 2/2003 | Williams et al. | |
| 6,517,533 B1 | 2/2003 | Swaminathan | |
| 6,522,926 B1 | 2/2003 | Kieval et al. | |
| 6,527,739 B1 | 3/2003 | Bigus et al. | |
| 6,527,765 B2 | 3/2003 | Kelman et al. | |
| 6,537,271 B1 | 3/2003 | Murray et al. | |
| 6,540,734 B1 | 4/2003 | Chiu et al. | |
| 6,542,781 B1 | 4/2003 | Koblish et al. | |
| 6,551,309 B1 | 4/2003 | LePivert | |
| 6,562,034 B2 | 5/2003 | Edwards et al. | |
| 6,575,933 B1 | 6/2003 | Wittenberger et al. | |
| 6,602,246 B1 | 8/2003 | Joye et al. | |
| 6,602,247 B2 | 8/2003 | Lalonde | |
| 6,610,083 B2 | 8/2003 | Keller et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,640,120 B1 | 10/2003 | Swanson et al. | |
| 6,648,878 B2 | 11/2003 | Lafontaine | |
| 6,648,879 B2 | 11/2003 | Joye et al. | |
| 6,666,858 B2 | 12/2003 | Lafontaine | |
| 6,673,066 B2 | 1/2004 | Werneth | |
| 6,685,648 B2 | 2/2004 | Flaherty et al. | |
| 6,685,732 B2 | 2/2004 | Kramer | |
| 6,706,037 B2 | 3/2004 | Zvuloni et al. | |
| 6,709,431 B2 | 3/2004 | Lafontaine | |
| 6,711,444 B2 | 3/2004 | Koblish | |
| 6,736,835 B2 | 5/2004 | Pellegrino et al. | |
| 6,755,823 B2 | 6/2004 | Lalonde | |
| 6,786,900 B2 | 9/2004 | Joye et al. | |
| 6,786,901 B2 | 9/2004 | Joye et al. | |
| 6,807,444 B2 | 10/2004 | Tu et al. | |
| 6,811,550 B2 | 11/2004 | Holland et al. | |
| 6,824,543 B2 | 11/2004 | Lentz | |
| 6,845,267 B2 | 1/2005 | Harrison et al. | |
| 6,850,801 B2 | 2/2005 | Kieval et al. | |
| 6,869,431 B2 | 3/2005 | Maguire et al. | |
| 6,875,209 B2 | 4/2005 | Zvuloni et al. | |
| 6,885,888 B2 | 4/2005 | Rezai | |
| 6,893,436 B2 | 5/2005 | Woodard et al. | |
| 6,905,510 B2 | 6/2005 | Saab | |
| 6,908,462 B2 | 6/2005 | Joye et al. | |
| 6,917,834 B2 | 7/2005 | Koblish et al. | |
| 6,923,808 B2 | 8/2005 | Taimisto | |
| 6,929,639 B2 | 8/2005 | Lafontaine | |
| 6,939,346 B2 | 9/2005 | Kannenberg et al. | |
| 6,949,097 B2 | 9/2005 | Stewart et al. | |
| 6,955,174 B2 | 10/2005 | Joye et al. | |
| 6,972,015 B2 | 12/2005 | Joye et al. | |
| 6,981,382 B2 | 1/2006 | Lentz et al. | |
| 6,989,009 B2 | 1/2006 | Lafontaine | |
| 7,001,378 B2 | 2/2006 | Yon et al. | |
| 7,022,120 B2 | 4/2006 | Lafontaine | |
| 7,060,062 B2 | 6/2006 | Joye et al. | |

(56) References Cited

U.S. PATENT DOCUMENTS

| | | |
|---|---|---|
| 7,081,112 B2 | 7/2006 | Joye et al. |
| 7,081,115 B2 | 7/2006 | Taimisto |
| 7,101,368 B2 | 9/2006 | Lafontaine |
| 7,149,574 B2 | 12/2006 | Yun et al. |
| 7,156,840 B2 | 1/2007 | Lentz et al. |
| 7,162,303 B2 | 1/2007 | Levin et al. |
| 7,172,589 B2 | 2/2007 | Lafontaine |
| 7,189,227 B2 | 3/2007 | Lafontaine |
| 7,221,979 B2 | 5/2007 | Zhou et al. |
| 7,288,089 B2 | 10/2007 | Yon et al. |
| 7,300,433 B2 | 11/2007 | Lane et al. |
| 7,306,590 B2 | 12/2007 | Swanson |
| 7,357,797 B2 | 4/2008 | Ryba |
| 7,381,200 B2 | 6/2008 | Katoh et al. |
| 7,387,126 B2 | 6/2008 | Cox et al. |
| 7,390,894 B2 | 6/2008 | Weinshilboum et al. |
| 7,449,018 B2 | 11/2008 | Kramer |
| 7,487,780 B2 | 2/2009 | Hooven |
| 7,507,233 B2 | 3/2009 | Littrup et al. |
| 7,556,624 B2 | 7/2009 | Laufer et al. |
| 7,604,631 B2 | 10/2009 | Reynolds |
| 7,617,005 B2 | 11/2009 | Demarais et al. |
| 7,620,451 B2 | 11/2009 | Demarais et al. |
| 7,641,679 B2 | 1/2010 | Joye et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,758,571 B2 | 7/2010 | Saadat |
| 7,778,703 B2 | 8/2010 | Gross et al. |
| 7,785,289 B2 | 8/2010 | Rios et al. |
| 7,861,725 B2 | 1/2011 | Swanson |
| 7,972,327 B2 | 7/2011 | Eberl et al. |
| 8,012,147 B2 | 9/2011 | Lafontaine |
| 8,062,289 B2 | 11/2011 | Babaev |
| 8,080,006 B2 | 12/2011 | Lafontaine et al. |
| 8,088,125 B2 | 1/2012 | Lafontaine |
| 8,123,741 B2 | 2/2012 | Marrouche et al. |
| 8,128,617 B2 | 3/2012 | Bencini et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,261 B2 * | 5/2012 | Watson ............ A61M 25/1006 606/21 |
| 8,439,909 B2 | 5/2013 | Wang et al. |
| 8,469,919 B2 | 6/2013 | Ingle et al. |
| 8,473,067 B2 | 6/2013 | Hastings et al. |
| 8,475,441 B2 | 7/2013 | Babkin et al. |
| 8,480,663 B2 | 7/2013 | Ingle et al. |
| 8,480,664 B2 | 7/2013 | Watson et al. |
| 8,663,211 B2 | 3/2014 | Fourkas et al. |
| 8,777,943 B2 | 7/2014 | Mayse et al. |
| 9,101,343 B2 | 8/2015 | Duong et al. |
| 9,402,676 B2 | 8/2016 | Babkin et al. |
| 2002/0045893 A1 | 4/2002 | Lane et al. |
| 2002/0120258 A1 | 8/2002 | Lalonde |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0036752 A1 | 2/2003 | Joye et al. |
| 2003/0050635 A1 | 3/2003 | Truckai et al. |
| 2003/0050681 A1 | 3/2003 | Pianca et al. |
| 2003/0060762 A1 | 3/2003 | Zvuloni et al. |
| 2003/0060858 A1 | 3/2003 | Kieval et al. |
| 2003/0074039 A1 | 4/2003 | Puskas |
| 2003/0088189 A1 | 5/2003 | Tu et al. |
| 2003/0088240 A1 | 5/2003 | Saadat |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danek et al. |
| 2004/0010289 A1 | 1/2004 | Biggs et al. |
| 2004/0024392 A1 | 2/2004 | Lewis et al. |
| 2004/0215186 A1 | 10/2004 | Cornelius et al. |
| 2004/0243119 A1 | 12/2004 | Lane et al. |
| 2004/0267250 A1 | 12/2004 | Yon et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0209587 A1 | 9/2005 | Joye et al. |
| 2005/0228460 A1 | 10/2005 | Levin et al. |
| 2005/0240117 A1 | 10/2005 | Zvuloni et al. |
| 2006/0084962 A1 | 4/2006 | Joye et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212027 A1 | 9/2006 | Marrouche et al. |
| 2006/0235374 A1 * | 10/2006 | Mandel ................ A61B 18/02 606/20 |
| 2006/0247611 A1 | 11/2006 | Abboud et al. |
| 2006/0271111 A1 | 11/2006 | Demarais et al. |
| 2007/0049924 A1 | 3/2007 | Rahn |
| 2007/0093710 A1 | 4/2007 | Maschke |
| 2007/0129720 A1 | 6/2007 | Demarais et al. |
| 2007/0185445 A1 | 8/2007 | Nahon et al. |
| 2007/0265687 A1 | 11/2007 | Deem et al. |
| 2007/0299433 A1 | 12/2007 | Williams et al. |
| 2008/0097251 A1 | 4/2008 | Babaev |
| 2008/0171974 A1 | 7/2008 | Lafontaine et al. |
| 2008/0208182 A1 | 8/2008 | Lafontaine et al. |
| 2008/0300584 A1 | 12/2008 | Lentz et al. |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0036948 A1 | 2/2009 | Levin et al. |
| 2009/0171333 A1 | 7/2009 | Hon |
| 2009/0182316 A1 | 7/2009 | Bencini |
| 2009/0182317 A1 | 7/2009 | Bencini |
| 2009/0209949 A1 | 8/2009 | Ingle et al. |
| 2009/0221955 A1 | 9/2009 | Babaev |
| 2009/0281533 A1 | 11/2009 | Ingle et al. |
| 2009/0287202 A1 | 11/2009 | Ingle et al. |
| 2009/0299355 A1 | 12/2009 | Bencini et al. |
| 2010/0049184 A1 | 2/2010 | George et al. |
| 2010/0069900 A1 | 3/2010 | Shirley et al. |
| 2010/0100087 A1 | 4/2010 | Mazzone et al. |
| 2010/0106148 A1 | 4/2010 | Joye et al. |
| 2010/0114269 A1 | 5/2010 | Wittenberger et al. |
| 2010/0125266 A1 | 5/2010 | Deem et al. |
| 2010/0130970 A1 | 5/2010 | Williams et al. |
| 2010/0137860 A1 | 6/2010 | Demarais et al. |
| 2010/0137952 A1 | 6/2010 | Demarais et al. |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0198203 A1 | 8/2010 | Kuck et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249766 A1 | 9/2010 | Saadat |
| 2010/0256621 A1 | 10/2010 | Babkin et al. |
| 2010/0280507 A1 | 11/2010 | Babkin et al. |
| 2011/0125143 A1 | 5/2011 | Gross et al. |
| 2011/0152855 A1 | 6/2011 | Mayse et al. |
| 2011/0257642 A1 | 10/2011 | Griggs, III |
| 2011/0263921 A1 | 10/2011 | Vrba et al. |
| 2011/0270238 A1 | 11/2011 | Rizq et al. |
| 2011/0282272 A1 | 11/2011 | Lafontaine |
| 2012/0029509 A1 | 2/2012 | Smith |
| 2012/0029511 A1 | 2/2012 | Smith et al. |
| 2012/0089047 A1 | 4/2012 | Ryba et al. |
| 2012/0109021 A1 | 5/2012 | Hastings et al. |
| 2012/0123261 A1 | 5/2012 | Jenson et al. |
| 2012/0130289 A1 | 5/2012 | Demarais et al. |
| 2012/0130345 A1 | 5/2012 | Levin et al. |
| 2012/0130360 A1 | 5/2012 | Buckley et al. |

(56) References Cited

U.S. PATENT DOCUMENTS

| | | | |
|---|---|---|---|
| 2012/0130368 A1 | 5/2012 | Jenson | |
| 2012/0136417 A1 | 5/2012 | Buckley et al. | |
| 2012/0136418 A1 | 5/2012 | Buckley et al. | |
| 2012/0143097 A1 | 6/2012 | Pike, Jr. | |
| 2012/0143177 A1 | 6/2012 | Avitall | |
| 2012/0150267 A1 | 6/2012 | Buckley et al. | |
| 2012/0172837 A1 | 7/2012 | Demarais et al. | |
| 2012/0253336 A1 | 10/2012 | Littrup et al. | |
| 2012/0277823 A1* | 11/2012 | Gerber | A61N 1/36132 607/46 |
| 2013/0090650 A1 | 4/2013 | Jenson et al. | |
| 2013/0123770 A1 | 5/2013 | Smith | |
| 2013/0184696 A1 | 7/2013 | Fourkas et al. | |
| 2013/0345688 A1 | 12/2013 | Babkin et al. | |
| 2014/0046313 A1 | 2/2014 | Pederson et al. | |
| 2014/0066914 A1 | 3/2014 | Lafontaine | |
| 2014/0276724 A1 | 9/2014 | Goshayeshgar | |
| 2014/0276728 A1 | 9/2014 | Goshayeshgar | |
| 2014/0276811 A1 | 9/2014 | Koblish et al. | |
| 2015/0105764 A1 | 4/2015 | Rizq et al. | |

FOREIGN PATENT DOCUMENTS

| | | |
|---|---|---|
| EP | 0655225 | 5/1995 |
| EP | 0955012 | 11/1999 |
| EP | 1129670 | 9/2001 |
| EP | 1164963 | 1/2002 |
| EP | 1389477 | 2/2004 |
| EP | 1502553 | 2/2005 |
| EP | 1559362 | 8/2005 |
| EP | 2558016 | 2/2013 |
| EP | 2598070 | 6/2013 |
| EP | 2598071 | 6/2013 |
| EP | 2608837 | 7/2013 |
| GB | 228367 | 2/1925 |
| GB | 1422535 | 1/1976 |
| GB | 2289414 | 11/1995 |
| SU | 718099 | 2/1980 |
| SU | 1153901 | 5/1985 |
| SU | 1329781 | 8/1987 |
| SU | 1378835 | 3/1988 |
| SU | 1771725 | 10/1992 |
| WO | WO1994007446 | 4/1994 |
| WO | WO-1995025472 | 9/1995 |
| WO | WO1995031142 | 11/1995 |
| WO | WO-199725011 | 7/1997 |
| WO | WO-1997036548 | 10/1997 |
| WO | WO1998042403 | 10/1998 |
| WO | WO-1999/00060 | 1/1999 |
| WO | WO-199905979 | 2/1999 |
| WO | WO-1999027862 | 6/1999 |
| WO | WO2000047118 | 8/2000 |
| WO | WO-2001022897 | 4/2001 |
| WO | WO-2001064145 | 9/2001 |
| WO | WO-2001070114 | 9/2001 |
| WO | WO-2002000128 | 1/2002 |
| WO | WO-2002004042 | 1/2002 |
| WO | WO-2002007625 | 1/2002 |
| WO | WO-2002007628 | 1/2002 |
| WO | WO-2002013710 | 2/2002 |
| WO | WO2002015807 | 2/2002 |
| WO | WO-2002058576 | 8/2002 |
| WO | WO-2003020334 | 3/2003 |
| WO | WO2003022167 | 3/2003 |
| WO | WO-2003061496 | 7/2003 |
| WO | WO2003082080 | 10/2003 |
| WO | WO-2005030072 | 4/2005 |
| WO | WO-2005038357 | 4/2005 |
| WO | WO-2005041748 | 5/2005 |
| WO | WO-2005110528 | 11/2005 |
| WO | WO-2006041881 | 4/2006 |
| WO | WO-2006096272 | 9/2006 |
| WO | WO2006105121 | 10/2006 |
| WO | WO-2006124177 | 11/2006 |
| WO | WO-2007008954 | 1/2007 |
| WO | WO2007078997 | 7/2007 |
| WO | WO2008049084 | 4/2008 |
| WO | WO-2008131037 | 10/2008 |
| WO | WO-2011056684 | 5/2011 |
| WO | WO-2011082278 | 7/2011 |
| WO | WO-2011082279 | 7/2011 |
| WO | WO-2012016135 | 2/2012 |
| WO | WO-2012016137 | 2/2012 |
| WO | WO-2012058430 | 5/2012 |
| WO | WO-2013074683 | 5/2013 |
| WO | WO-2013106859 | 7/2013 |
| WO | WO2014150204 | 9/2014 |
| WO | WO2014158727 | 10/2014 |
| WO | WO2014164445 | 10/2014 |

OTHER PUBLICATIONS

510K Summary of CryoGen Cryosurgery System, filed with FDA Jul. 3, 1997—approved Oct. 1, 1997, 1997, 5 pages.
CO2/Gas Composite Regulator, Sep. 6, 2011, 2 pages. <http://www.genuineinnovations.com/composite-regulator.html>.
CryoGen SS&E: HerOption Uterine Cryoblatin Therapy System, filed with FDA Aug. 15, 2000—approved Apr. 20, 2001, 1999, 84 pages.
International Search Report and Written Opinion dated Apr. 12, 2012, International Application No. PCT/US2011/057514, 15 pages.
International Search Report and Written Opinion dated Apr. 13, 2012, International Application No. PCT/US2011/057502, 14 pages.
International Search Report and Written Opinion dated Dec. 28, 2011, International Application No. PCT/US2011/057508, 12 pages.
International Search Report and Written Opinion dated Feb. 14, 2012, International Application No. PCT/US2011/057504, 12 pages.
International Search Report and Written Opinion dated Feb. 20, 2012, International Application No. PCT/US2011/057483, 11 pages.
International Search Report and Written Opinion dated Feb. 23, 2012, International Application No. PCT/US2011/057490, 14 pages.
International Search Report and Written Opinion dated Feb. 6, 2012, International Application No. PCT/US2011/057497, 12 pages.
International Search Report and Written Opinion dated Jun. 13, 2013, International Application No. PCT/US2012/063411, 13 pages.
International Search Report and Written Opinion dated Mar. 16, 2012, International Application No. PCT/US2011/057511, 16 pages.
International Search Report and Written Opinion dated Mar. 9, 2012, International Application No. PCT/US2011/057523, 15 pages.
Lura Harrison, Ph.D. et al., "Cryosurgical Ablation of the A-V Node-His Bundle—A New Method for Producing A-V Block," Circulation, vol. 55, 1977 pp. 463-470.
Medical Grade Gas Dispenser, Sep. 6, 2011, 1 page, <http://www.abd-inc.com/Frame-904990-page1namepage904990.html?refresh=1205442262133>.
Sesia G. et al., "The use of nitrous oxide as a freezing agent in cryosurgery of the prostate," International Surgery [Int Surg], vol. 53, 1970, pp. 82-90.
Special Order Only Thermal Dilution Injector, Obsolete Product, Sep. 6, 2011, 1 page, <http://www.abd-inc.com/Frame-904990-page1namepage904990.html?refresh=1205442262133>.
Torre, Douglas, MD, "Alternate Cryogens for Cryosurgery," J. Derm. Surgery, Jun. 1975, pp. 56-58.
Voĭtyna SV, "Cryocatheter-tourniquet," Meditsinskaia Tekhnika [Med Tekh], vol. 6, 1976, pp. 47-48.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

(56) References Cited

OTHER PUBLICATIONS

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news--latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n. l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison Awards[TM]" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio—Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Interv Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." Am. J. Roentgenol,174: 1592-1594 (2000).

Han, Y.-M, et al., "Renal artery ebolization with diluted hot contrast medium: An experimental study." J Vasc Interv Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

(56) References Cited

OTHER PUBLICATIONS

Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot$^{TM}$ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
European Search Report for European Application No. 13159256, dated Oct. 17, 2013, 6 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.

(56) References Cited

OTHER PUBLICATIONS

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

DiBona, Gerald F. et al., "Neural Control of Renal Function," Physiological Reviews, vol. 77, No. 1, Jan. 1997, The American Physiological Society 1997, pp. 75-197.

DiBona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361;9.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009.

Schlaich, M.P. et al., "Renal Denervation as a Therapeutic Approach for Hypertension: Novel Implictions for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16:160.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.

Opposition to European Patent No. 2465470, Granted Oct. 28, 2015, Date of Opposition Jul. 27, 2016, 34 pp.

Pieper, et al., "Design and Implementation of a New Computerized System for Intraoperative Cardiac Mapping" Journal of Applied Physiology, 1991, vol. 71 (4), pp. 1529-1539.

Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

U.S. Appl. No. 11/363,867, filed Feb. 27, 2006, 70 pp.
U.S. Appl. No. 60/813,589, filed Dec. 29, 2005, 62 pp.
U.S. Appl. No. 60/852,787, filed Oct. 18, 2006, 112 pp.
Ureter, https://en.wikipedia.org/wiki/Ureter, Jun. 2016, 6 pp.

* cited by examiner

MONITORING AND CONTROLLING INTERNALLY ADMINISTERED CRYOTHERAPY

TECHNICAL FIELD

The present technology relates generally to cryotherapy, such as monitoring and controlling cryotherapy administered via a refrigerant-cooled cryotherapeutic element positioned within a patient's body.

BACKGROUND

Cryotherapy is a useful treatment modality for many types of medical procedures. In some cases, it is desirable to administer cryotherapy from within a patient's body, such as from within a body lumen. Internal administration of cryotherapy can be advantageous, for example, in at least some neuromodulation procedures. These procedures can include percutaneously introducing a cryotherapeutic element into a patient and then advancing a catheter shaft carrying the cryotherapeutic element along an intravascular path to a suitable treatment location. Once positioned at the treatment location, the cryotherapeutic element can be cooled to modulate nearby nerves. The cooling caused by the cryotherapeutic element, for example, can reduce undesirable local or systemic sympathetic neural activity and thereby achieve various therapeutic benefits.

Cryotherapy may have certain advantages relative to other modalities for executing some types of treatments. For example, in the case of neuromodulation, adhesion associated with freezing may assist in achieving uniform and stable contact between a cryotherapeutic element and surrounding tissue for a sustained period of time while neuromodulation occurs. As another example, cryotherapy may be relatively unlikely to cause stenosis at an intravascular treatment location. As yet another example, cryotherapy may tend to provide a beneficial analgesic effect and, therefore, may reduce the need for analgesic medication. Technical challenges associated with cryotherapy, however, can make these and other advantages difficult to realize. Accordingly, innovation in this field to address such challenges has significant potential to make cryotherapy a more effective, efficient, and widely used tool for improving the health of patients.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1A:
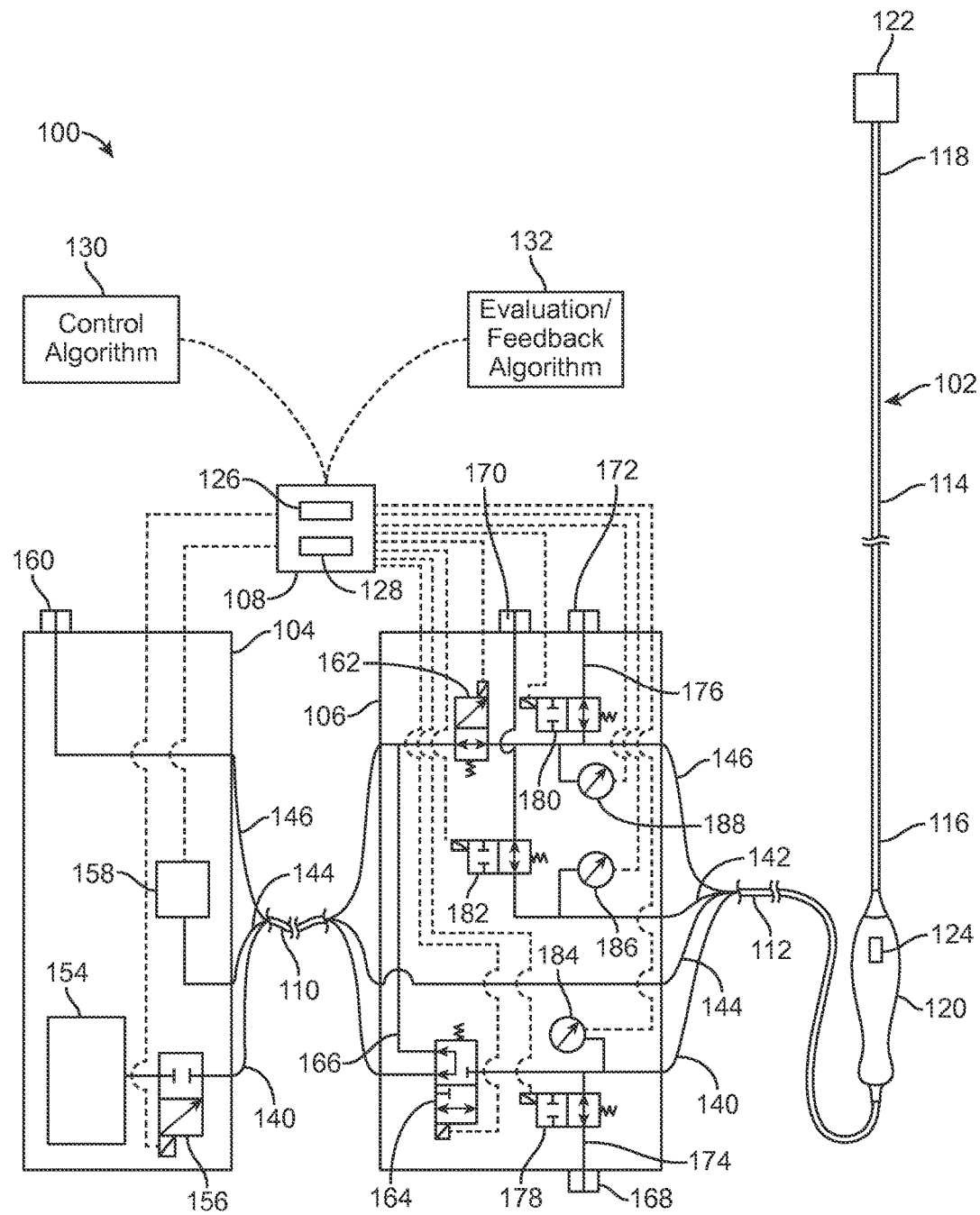
FIG. 1A is a partially schematic perspective view illustrating a cryotherapy system including a catheter having a cryotherapeutic element configured in accordance with an embodiment of the present technology.

At least some embodiments of the present technology relate to monitoring one or more variables (e.g., pressure and/or temperature) that change in response to operation of a cryotherapeutic system and controlling operation of the system based on information gathered from this monitoring. In this way, the reliability, efficacy, and/or other aspects of a treatment performed using the system may be enhanced. One example of a treatment compatible with at least some embodiments of the present technology includes expanding refrigerant within a balloon of a cryotherapeutic element while the cryotherapeutic element is operably positioned within a body lumen. The expanding refrigerant can cause the balloon to press against an inner surface of a wall of the body lumen. It can further cause heat to be drawn away from the wall via the Joule-Thomson effect alone or in combination with evaporative cooling. Cooling by expanding refrigerant is therapeutically advantageous due, for example, to its capacity for removing heat rapidly and efficiently. In the context of internally administered cryotherapy, however, some clinicians may be concerned that this manner of cooling carries a risk of causing a gas embolism, such as if a balloon were to rupture during a treatment.

To address the perceived risk of causing a gas embolism, some conventional cryotherapeutic elements include a double-walled balloon. During use of such cryotherapeutic elements, refrigerant may expand within an inner balloon wall and, if a leak of refrigerant through the inner balloon wall should occur, an outer balloon wall may help to prevent leaked refrigerant from escaping into a patient's body. Although potentially useful for reducing the possibility of refrigerant leakage into a patient's body, double-walled balloons can have certain disadvantages. For example, double-walled balloons may have inconsistent thermal conductivity and relatively low average thermal conductivity, making them potentially poorly suited for cooling tissue precisely and adequately. As another example, double-walled balloons tend to be considerably more bulky than single-walled balloons. Thus, double-walled balloons may not be suitable for use with small-diameter sheaths and/or within small-diameter body lumens.

Cryotherapeutic systems and devices configured in accordance with embodiments of the present technology and associated methods can at least partially address one or more of the potential disadvantages described above and/or other potential disadvantages associated with conventional technologies, whether or not stated herein. A cryotherapeutic system configured in accordance with a particular embodiment includes a catheter having an elongate shaft and a cryotherapeutic element operably connected to the shaft. The system further includes a supply line that carries high-pressure refrigerant toward the cryotherapeutic element, and an exhaust line that carries expanded refrigerant away from the cryotherapeutic element. The system can be controlled so as to be capable of detecting one or more of several types of errors that could, in rare circumstances, lead to the release of a clinically significant quantity of refrigerant into a patient's body. In response to this detection, a flow of refrigerant along the supply line can be at least partially shut off. Aspects of the manner in which the system is controlled may allow error detection and response to occur extremely rapidly and without unduly interfering with normal operation of the system. Thus, if a balloon failure or another significant type of error were to occur, the system can be controlled so as to cause the amount of refrigerant released into a patient's body to be relatively small and of negligible or at least low clinical significance.

Systems configured in accordance with at least some embodiments of the present technology include a cryotherapeutic element having a single-walled balloon. In an example of such a system, enhanced error detection and response may take the place of an outer balloon wall for reducing the possibility of clinically significant refrigerant leakage into a patient's body. Systems configured in accordance with other embodiments can include a cryotherapeutic element having a balloon with two or more walls. In an example of such a system, enhanced error detection and response may supplement the effect of one or more outer balloon walls for reducing the possibility of clinically significant refrigerant leakage into a patient's body. A system including both enhanced error detection and response and one or more outer balloon walls, for example, can rely on these features as redundant mechanisms for reducing the possibility of clinically significant refrigerant leakage into a patient's body. Although completely eliminating the risk of clinically significant refrigerant leakage into a patient's body is unlikely, systems configured in accordance with at least some embodiments of the present technology may cause this risk to be medically justified in view of the significant advantages of cryotherapeutic cooling by expanding refrigerant over other treatment modalities.

Specific details of several embodiments of the present technology are described herein with reference to FIGS. 1A-4. Although many of the embodiments are described herein with respect to devices, systems, and methods for intravascular renal neuromodulation, other applications and other embodiments in addition to those described herein are within the scope of the present technology. For example, at least some embodiments may be useful for neuromodulation within a body lumen other than a vessel, for extravascular neuromodulation, for non-renal neuromodulation, and/or for use in therapies other than neuromodulation. It should understood, in general, that other embodiments in addition to those disclosed herein are within the scope of the present technology. Furthermore, embodiments of the present technology can have different configurations, components, and/or procedures than those disclosed herein. Moreover, a person of ordinary skill in the art will understand that embodiments of the present technology can have configurations, components, and/or procedures in addition to those disclosed herein and that these and other embodiments can be without several of the configurations, components, and/or procedures disclosed herein without deviating from the present technology.

As used herein, the terms "distal" and "proximal" define a position or direction with respect to a clinician or a clinician's control device (e.g., a handle of a catheter). The terms "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

Selected Examples of Cryotherapeutic Systems

FIG. 1A is a partially schematic perspective view of a cryotherapeutic system 100 (e.g., a cryotherapeutic neuromodulation system) configured in accordance with an embodiment of the present technology. The system 100 can include a catheter 102, a console 104, a fluidics unit 106, and a controller 108 operably connected to one another. In the illustrated embodiment, the system 100 includes a first cable 110 extending between the console 104 and the fluidics unit 106, and a second cable 112 extending between the fluidics unit 106 and the catheter 102. The console 104 can occupy a relatively large volume (e.g., greater than 0.2 cubic meter) and be configured to be positioned a significant distance (e.g., greater than 2 meters) from the catheter 102. In contrast, the fluidics unit 106 can occupy a relatively small volume (e.g., less than 5,000 cubic centimeters) and be configured to be positioned closer (e.g., less than 1 meter) to the catheter 102. In other embodiments, the catheter 102, the console 104, and/or the fluidics unit 106 can have other suitable characteristics and/or other suitable arrangements. For example, the fluidics unit 106 can be integrated into the console 104 or integrated into the catheter 102.

With reference again to FIG. 1A, the catheter 102 can include an elongate shaft 114 having a proximal end portion 116 and a distal end portion 118. The catheter 102 can further include a handle 120 and a cryotherapeutic element 122 (e.g., a cryotherapeutic neuromodulation element—shown schematically) operably connected to the shaft 114. The shaft 114 can be configured to locate the cryotherapeutic element 122 at a treatment location within a body lumen, such as a suitable blood vessel, duct, airway, or other naturally occurring lumen within the human body. For example, the shaft 114 can be configured to locate the cryotherapeutic element 122 intravascularly at a treatment location proximate (e.g., in or near) a renal artery or renal ostium when the catheter 102 is used for renal neuromodulation. The cryotherapeutic element 122 can be configured to provide or support a cryotherapeutic treatment (e.g., a cryotherapeutic neuromodulation treatment) when operably positioned at the treatment location.

The shaft 114 and the cryotherapeutic element 122 can be configured to be slidably disposed within a sheath (not shown) while the catheter 102 is being deployed within a body lumen. The inside diameter of the sheath, for example, can be sized to accommodate (e.g., snugly accommodate) the shaft 114 when the shaft 114 is 2, 3, 4, 5, 6, or 7 French or another suitable size. Deployment of the catheter 102 can include, for example, percutaneously inserting a guide wire (not shown) into a body lumen of a patient, percutaneously inserting the catheter 102 into the body lumen over the guide wire, and advancing the catheter 102 along the guide wire until the cryotherapeutic element 122 reaches a suitable treatment location. As another example, the catheter 102 can be steerable or non-steerable and configured for deployment without a guide wire (e.g., using a guide catheter). As yet another example, the catheter 102 can be configured for deployment via a guide sheath (not shown) instead of a guide wire.

In some embodiments, the handle 120 includes a control device 124 (e.g., a switch, a dial, a button, a touch screen, or a slider) configured to initiate, terminate, and/or adjust operation of one or more components of the catheter 102 directly and/or via another component of the system 100 (e.g., via the controller 108). In other embodiments, the control device 124 can be absent or can have another suitable location within the system 100, such as within the fluidics unit 106. The controller 108 can include processing circuitry 126 (e.g., one or more microprocessors) and memory 128 and can be configured to execute an automated control algorithm 130 and/or to receive control instructions from an operator (not shown). Furthermore, the controller 108 can be configured to provide information to an operator before, during, and/or after a treatment procedure using an evaluation/feedback algorithm 132.

Figure 1B:
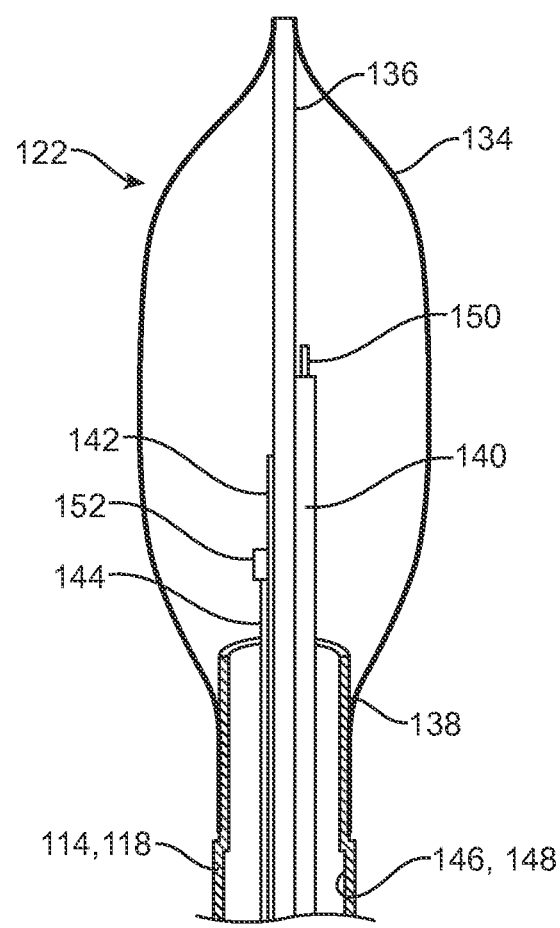
FIG. 1B is an enlarged cross-sectional side view of the cryotherapeutic element of the cryotherapeutic system shown in FIG. 1A.

FIG. 1B is an enlarged cross-sectional side view of the cryotherapeutic element 122. As shown in FIG. 1B, the cryotherapeutic element 122 can include a balloon 134 operably connected to the shaft 114. In the illustrated embodiment, the balloon 134 is a single-walled balloon. As discussed above, in other embodiments, the balloon 134 can be a multiple-walled balloon, such as a double-walled balloon. With reference to FIGS. 1A and 1B together, the catheter 102 can include a guide-wire conduit 136 extending distally from the shaft 114 through the cryotherapeutic element 122. The balloon 134 can be attached at one end to an outer circumference of the guide-wire conduit 136 and at an opposite end to the distal end portion 118 of the shaft 114. For example, the distal end portion 118 of the shaft 114 can include a stepped-down segment 138 and an end of the balloon 134 opposite to an end attached to the guide-wire conduit 136 can be attached to an outer surface of the stepped-down segment 138.

The catheter 102 can include a supply line 140, a monitoring line 142, a sensor lead 144, and an exhaust line 146 each operably connected to the cryotherapeutic element 122 and extending proximally from the cryotherapeutic element 122 along at least a portion of a length of the shaft 114. In some embodiments, the supply line 140, the monitoring line 142, the sensor lead 144, and the exhaust line 146 extend along the length of the shaft 114 all the way to the handle 120. In other embodiments, at least one of the supply line 140, the monitoring line 142, the sensor lead 144, and the exhaust line 146 branches off from the shaft 114 at a suitable location (e.g., a suitable extracorporeal location) distal to the handle 120. Refrigerant can flow through the supply line 140 toward the cryotherapeutic element 122. As shown in FIG. 1B, in the illustrated embodiment, the supply line 140, the monitoring line 142, and the sensor lead 144 extend through a main lumen 148 of the shaft 114. A remaining portion of the main lumen 148 can serve as the exhaust line 146. As shown in FIG. 1A, proximal to the handle 120, the exhaust line 146 can be separate from the supply line 140, the monitoring line 142, and the sensor lead 144. In other embodiments, the supply line 140, the monitoring line 142, the sensor lead 144, and the exhaust line 146 can be arranged in another suitable manner.

The cryotherapeutic element 122 can include an expansion orifice 150 at a distal end of the supply line 140. In operation, a pressure drop occurs when the refrigerant passes through the expansion orifice 150. The refrigerant expands and, in at least some cases, changes phase from liquid to gas within the balloon 134. The expansion of the refrigerant may resiliently or non-resiliently increase the volume or maintain an increased volume of the balloon 134 and may also cool the balloon 134 to a suitable temperature for cryotherapy. After expanding, the refrigerant can flow proximally away from the cryotherapeutic element 122 through the exhaust line 146. The cryotherapeutic element 122 can further include a temperature sensor 152 (e.g., a thermocouple), and the sensor lead 144 can be configured to carry a temperature signal from the temperature sensor 152 proximally along at least a portion of the length of the shaft 114. Similarly, the monitoring line 142 can be open at its distal end and configured to carry a pressure signal proximally along at least a portion of the length of the shaft 114.

The supply line 140, the monitoring line 142, the sensor lead 144, and the exhaust line 146 can extend from the cryotherapeutic element 122, through the shaft 114, and through the second cable 112 to the fluidics unit 106. The monitoring line 142 can terminate at the fluidics unit 106. The supply line 140, the sensor lead 144, and the exhaust line 146 can extend through the fluidics unit 106 to the console 104 and terminate at the console 104. The console 104 can include a refrigerant supply 154 operably connected to the supply line 140. The refrigerant supply 154 can include a cartridge (e.g., a single-use or multiple-use cartridge), a canister (e.g., a tank or a cylinder), or another suitable container (not shown) configured to hold refrigerant at high pressure. For example, the refrigerant supply 154 can be configured to contain $N_2O$ at a pressure of 750 psi or another suitable pressure for maintaining the $N_2O$ at least substantially in liquid phase at ambient temperature. In addition or alternatively, the refrigerant supply 154 can be configured to contain liquid $CO_2$, a liquid hydrofluorocarbon (e.g., FREON® refrigerant, R-410A, etc.), or another suitable refrigerant at the same or a different pressure.

The console 104 can include a first valve 156 (e.g., a supply valve) operably connected to the supply line 140 downstream from the refrigerant supply 154. The first valve 156 can be configured to default to a closed state and actuate (e.g., in response to instructions from the controller 108) to a regulated open state. The first valve 156 can be used, for example, as a primary mechanism for actively controlling the flow of refrigerant along the supply line 140 when the system 100 is operating normally. The console 104 can further include a signal processor 158 configured to receive a signal from the temperature sensor 152 via the sensor lead 144. The signal processor 158 can be configured to convert the received signal into a suitable format for communication to and use by the controller 108. A first outlet 160 of the console 104 can be operably connected to the exhaust line 146. The first outlet 160, for example, can vent directly to the atmosphere or be connected to an exhaust capturing device (not shown) and/or a facility-level exhaust line (also not shown).

The fluidics unit 106 can include a second valve 162 (e.g., an exhaust valve) operably connected to the exhaust line 146. The second valve 162 can default to a fully open state and actuate (e.g., in response to instructions from the controller 108) to a regulated open state. The fluidics unit 106 can further include a third valve 164 (e.g., a bleed valve) operably connected to the supply line 140. Extending from the third valve 164 to the exhaust line 146, the fluidics unit 106 can include a bleed line 166. The third valve 164 can be configured to default to a bleed state and actuate (e.g., in response to instructions from the controller 108) to a non-bleed state. When the third valve 164 is in the bleed state, a portion of the supply line 140 extending from the third valve 164 to the cryotherapeutic element 122 can be closed and a portion of the supply line 140 extending from the third valve 164 to the refrigerant supply 154 can be fluidically connected to the bleed line 166. When the third valve 164 is in the non-bleed state, the bleed line 166 can be closed and the portion of the supply line 140 extending from the third valve 164 to the cryotherapeutic element 122 can be fluidically connected to the portion of the supply line 140 extending from the third valve 164 to the refrigerant supply 154.

The fluidics unit 106 can include a second outlet 168, a third outlet 170, and a fourth outlet 172 operably connected to the supply line 140, the monitoring line 142, and the exhaust line 146, respectively. Extending between the supply line 140 and the second outlet 168, the fluidics unit 106 can include a first branch line 174. Similarly, extending between the exhaust line 146 and the fourth outlet 172, the fluidics unit 106 can include a second branch line 176. The fluidics unit 106 can further include a fourth valve 178 and a fifth valve 180 operably connected to the first branch line 174 and the second branch line 176, respectively. The fluidics unit 106 can still further include a sixth valve 182 operably connected to the monitoring line 142. The fourth valve 178, the fifth valve 180, and the sixth valve 182, individually, can be configured to default to a fully open state and actuate (e.g., in response to instructions from the controller 108) to a closed state. The first branch line 174 can connect to the supply line 140 at a junction downstream from the third valve 164. Similarly, the second branch line 176 can connect to the exhaust line 146 at a junction downstream from the second valve 162.

The fluidics unit 106 can also include a first pressure sensor 184 operably connected to the supply line 140 downstream from the third valve 164. Similarly, the fluidics unit 106 can include a second pressure sensor 186 operably connected to the monitoring line 142 downstream from the sixth valve 182. Also similarly, the fluidics unit 106 can include a third pressure sensor 188 operably connected to the exhaust line 146 downstream from the second valve 162. The first, second, and third pressure sensors 184, 186, 188 can be, for example, Model PX209-100G5V pressure transducers made by OMEGA Engineering Inc. (Stamford, Conn.) or another suitable type. Similar to the signal processor 158 of the console 104, the first, second, and third pressure sensors 184, 186, 188 can be configured to send monitoring information to the controller 108. The first and third pressure sensors 184, 188 can be configured to detect pressure within the supply line 140 and the exhaust line 146, respectively. The second pressure sensor 186 can be configured, in conjunction with the monitoring line 142, to monitor pressure within the cryotherapeutic element 122 and/or within a distal portion of the exhaust line 146.

The configurations of components, the arrangement of compounds, and/or other features of the system 100 shown in FIGS. 1A and 1B can be different in other embodiments. For example, in some embodiments, one or more of the first, second, third, and fourth outlets 160, 168, 170, 172 are merged. Additional details of numerous additional examples of cryotherapeutic systems configured in accordance with embodiments of the present technology are included in PCT International Publication No. WO2013/067421, which is incorporated herein by reference in its entirety.

Selected Examples of Cryotherapeutic Methods

Figure 2:
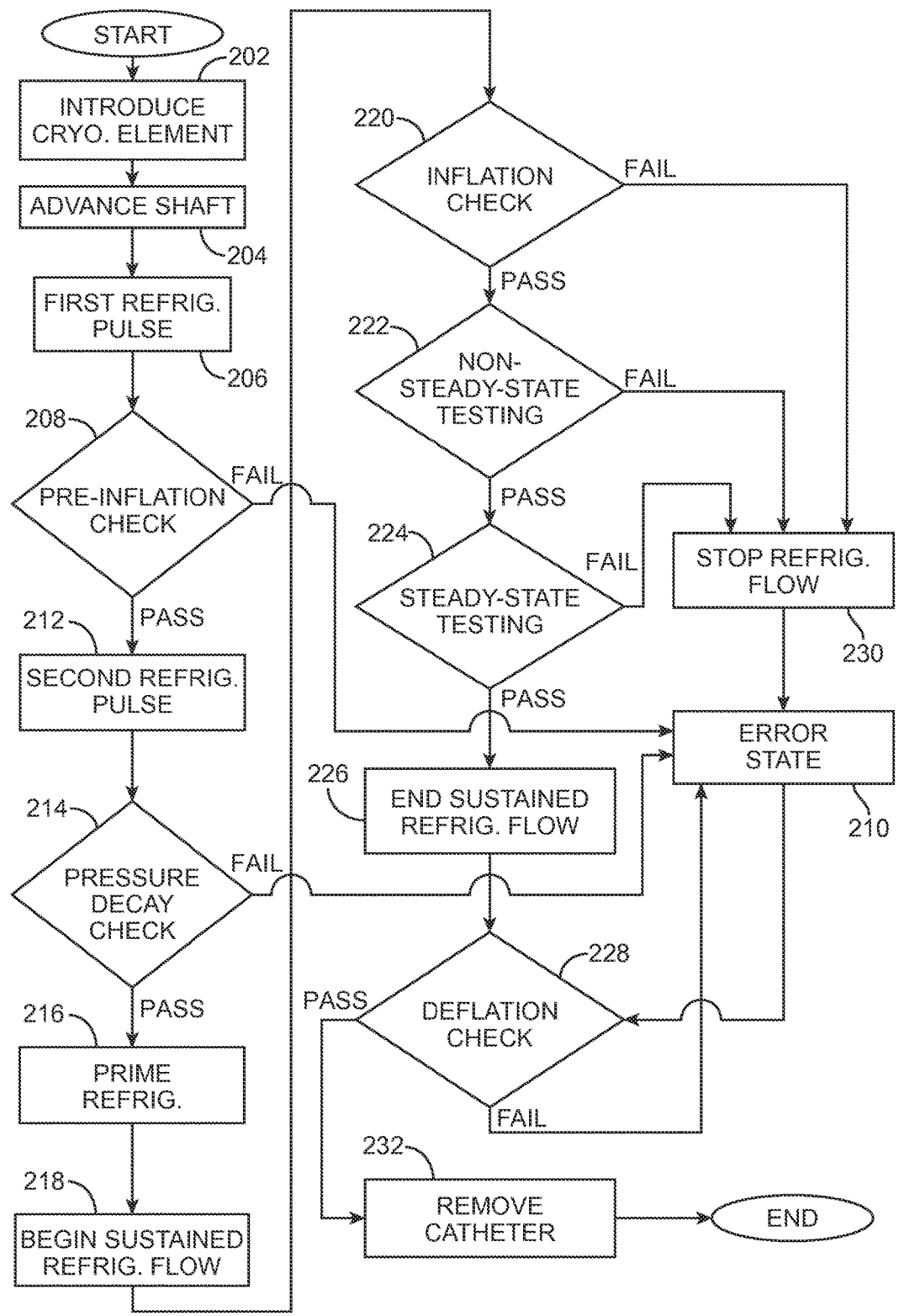
FIG. 2 is a flow chart illustrating a method for controlling the cryotherapeutic system shown in FIG. 1A in accordance with an embodiment of the present technology.

FIG. 2 is a flow chart illustrating a method 200 for controlling the system 100 in accordance with an embodiment of the present technology. With reference to FIGS. 1A-2 together, all or a suitable portion of the method 200 can be performed by the controller 108 using the processing circuitry 126 according to computer-readable instructions stored on the memory 128, such as in a non-transitory form. The method 200 can begin when a clinician introduces the cryotherapeutic element 122 (block 202) into a human patient. The shaft 114 can then be advanced (block 204) along a suitable catheterization path toward a treatment location within a body lumen of the patient. In at least the case of a renal neuromodulation procedure, the catheterization path can be an intravascular path (e.g., a femoral, radial, or brachial path) and the treatment location can be within a renal artery and/or a renal ostium.

While the shaft 114 is advanced, the first valve 156 can be closed, the third valve 164 can be in its bleed state, and the second, fourth, fifth, and sixth valves 162, 178, 180, 182 can be open. After the cryotherapeutic element 122 is positioned at the treatment location, the third valve 164 can be switched to its non-bleed state, the fourth valve 178 can be closed, and the first valve 156 can be opened briefly to allow a first pulse of refrigerant to be released (block 206) into the balloon 134 via the supply line 140. Before, at about the same time, or shortly after releasing the first pulse of refrigerant (block 206), the second, fifth, and sixth valves 162, 180, 182 can be closed to at least partially capture refrigerant within the balloon 134. While the refrigerant is captured within the balloon 134, a pre-inflation check (block 208) can be performed on the system 100. The pre-inflation check (block 208) can include measuring a pressure within the exhaust line 146 using the third pressure sensor 188 and determining if the measured pressure is within a range indicating that the balloon 134 is intact. This may detect leaks in the balloon 134 or other potential defects when the balloon 134 is inflated to a pressure less than a pressure that the second pressure sensor 186 would be capable of detecting due, for example, to a pressure drop associated with the monitoring line 142. Since it can be carried out while very little refrigerant is at risk of being released into a patient's body, the pre-inflation check (block 208) may serve as a useful initial check to test the basic structural integrity of the balloon 134 after the balloon 134 is positioned at the treatment location. If the system 100 fails all or a portion of the pre-inflation check (block 208), the system 100 can be put into an error state (block 210).

After the pre-inflation check (block 208), the method 200 can include releasing a second pulse of refrigerant (block 212) into the balloon 134 via the supply line 140 and again at least partially capturing the released refrigerant within the balloon 134. While refrigerant is captured within the balloon 134, a pressure-decay check (block 214) can be performed on the balloon 134. The pressure-decay check (block 214) can include measuring a pressure within the balloon 134 and/or within the distal portion of the exhaust line 146 via the monitoring line 142 using the second pressure sensor 186 and determining if the measured pressure is within a range indicating that the balloon 134 is intact. Releasing the second pulse of refrigerant (block 212) can include releasing a quantity of refrigerant that is greater (e.g., at least about 5, 10 or 15 times greater) than a quantity of refrigerant released when releasing the first pulse of refrigerant (block 206), but still less than a quantity that would be likely to cause a clinically significant gas embolism if leaked into a patient's body. Accordingly, the pressure-decay check (block 214) can serve as a useful secondary check to test the basic functional integrity of the balloon 134 under stress after the balloon 134 is positioned at the treatment location. As with the pre-inflation check (block 208), if the system 100 fails all or a portion of the pressure-decay check (block 214), the system 100 can be put into the error state (block 210).

The refrigerant introduced into the balloon 134 during the pre-inflation check (block 208) and the pressure-decay check (block 214) can be mostly or entirely gaseous upstream from the expansion orifice 150. For example, the refrigerant can be drawn from a gaseous headspace of the refrigerant supply 154. The use of gaseous rather than liquid refrigerant can facilitate relatively precise control over small, discrete refrigerant volumes. In some embodiments, releasing the first pulse of refrigerant (block 206) includes opening the first valve 156 for a period of time within a range from 5 milliseconds to 25 milliseconds, such as for about 15 milliseconds, and releasing the second pulse of refrigerant (block 212) includes opening the first valve 156 for a period of time within a range from 250 milliseconds to 450 milliseconds, such for about 350 milliseconds. In other embodiments, releasing the first pulse of refrigerant (block 206) and/or releasing the second pulse of refrigerant (block 212) can include opening the first valve 156 for other suitable periods of time depending, for example, on the type of refrigerant, the diameter of the catheter 102, the length of the catheter 102, the pressure of the refrigerant, the mechanical properties of the balloon 134, and/or the volume of the balloon 134.

In at least some cases, upon successful completion of the pre-inflation check (block 208) and the pressure-decay check (block 214), the basic structural integrity of the balloon 134 at varying levels of stress has been sufficiently confirmed. As this point, refrigerant downstream from the refrigerant supply 154 can be primed (block 216) so as to increase a liquid fraction of the refrigerant. Priming the refrigerant (block 216) can include moving the third valve 164 into its bleed state such that refrigerant from the refrigerant supply 154 bleeds through the first outlet 160. This can be useful, for example, to displace gas within a portion of the supply line 140 between the console 104 and the fluidics unit 106 with liquid refrigerant. Priming the refrigerant (block 216) can cause liquid refrigerant to be staged at a consistent position relatively near to the catheter 102. Delivery of the refrigerant from this point to the cryotherapeutic element 122 can be more precise, more reliable, and/or subject to less delay that it would be if liquid refrigerant were to be drawn directly from the refrigerant supply 154 or from inconsistent positions within the supply line 140. After priming the refrigerant (block 216), a sustained flow of refrigerant toward the cryotherapeutic element 122 via the supply line 140 can be initiated (block 218), such as by opening a fluidic connection between the refrigerant supply 154 and the supply line 140.

Initiating the sustained flow of refrigerant (block 218) can begin a treatment cycle during which the refrigerant directed toward the cryotherapeutic element 122 expands to cause cooling within the balloon 134. Expanding the directed refrigerant can also cause the balloon 134 to increase in volume and press against a wall of the body lumen. For example, an outer surface of the balloon 134 can be in direct contact with an inner surface of a wall of the body lumen and an inner surface of the balloon 134 can be in direct contact with the expanded refrigerant. The expanded refrigerant can flow away from the balloon 134 via the exhaust line 146. During the treatment cycle, the pressure within the cryotherapeutic element 122 and/or within the distal portion of the exhaust line 146 can be monitored via the monitoring line 142, and the temperature within the cryotherapeutic element 122 and/or within the distal portion of the exhaust line 146 can be monitored via the sensor lead 144.

The measured temperature, a variable based on the measured temperature (e.g., rate of change of the measured temperature), the measured pressure, a variable based on the measured pressure (e.g., rate of change of the measured pressure), another suitable variable, or a combination thereof can be checked or otherwise processed at suitable times during the treatment cycle. For example, the variable can be processed once at a single time (e.g., a single predetermined time) during the treatment cycle and/or processed repeatedly (e.g., at intervals) over the course of a time period (e.g., a predetermined time period) during the treatment cycle. As shown in FIG. 2, the method 200 can include subjecting the balloon 134 to an inflation check (block 220), to non-steady-state testing (block 222), and to steady-state testing (block 224), which are further described below with reference to FIG. 3. Thereafter, the sustained flow of refrigerant to the cryotherapeutic element 122 can be stopped (block 226) and the balloon 134 can be subjected to a deflation check (block 228), which is also further described below with reference to FIG. 3.

The non-steady-state testing (block 222) and the steady-state testing (block 224) can correspond to different monitoring windows during which the controller 108 executes different feedback loops. For example, the executed feedback loops can be different with respect to their upper and/or lower thresholds for a measured variable. If an error occurs during the inflation check (block 220), the non-steady-state testing (block 222), or the steady-state testing (block 224), the flow of refrigerant toward the cryotherapeutic element 122 can be stopped (block 230) and, at the same time or shortly thereafter, the system 100 can be put into the error state (block 210). If an error occurs during the deflation check (block 228), the system 100 can be put directly into the error state (block 210). When the system 100 is in the error state (block 210), the first through sixth valves 156, 162, 164, 178, 180, 182 can return to their default states and an error indicator can be displayed to a clinician. Thereafter, the balloon 134 can be subjected to the deflation check (block 228), which can be a repeat deflation check (block 228) if the balloon 134 did not pass a previous deflation check (block 228). When the balloon 134 passes the deflation check (block 228), either at the end of an error-free treatment cycle or after the system 100 is moved into the error state (block 210), the system 100 can indicate to a clinician that it is safe to remove the catheter 102 from a patient (block 232).

Figure 3:
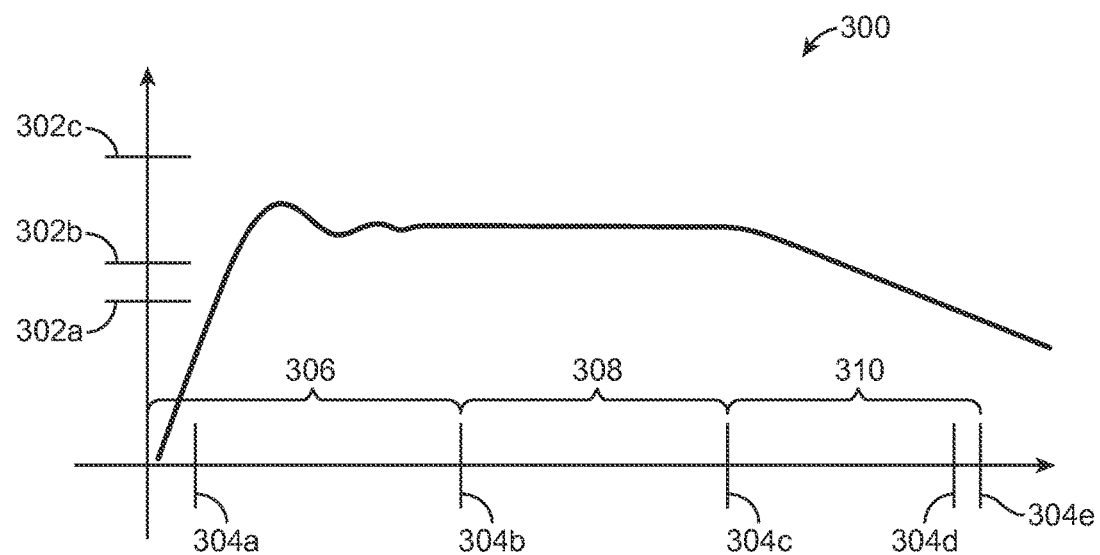
FIG. 3 is a plot of measured pressure (y-axis) relative to time (x-axis) during a neuromodulation procedure in accordance with an embodiment of the present technology.

FIG. 3 is a plot 300 of measured pressure (y-axis) within the cryotherapeutic element 122 and/or within the distal portion of the exhaust line 146 relative to time (x-axis) during a neuromodulation procedure in accordance with an embodiment of the present technology. With reference to FIGS. 2 and 3 together, along the y-axis of the plot 300 are a series of successively greater pressures (individually identified as pressures 302a-302c). Along the x-axis of the plot 300 are a series of successively greater times (individually identified as times 304a-304e). The time at the origin of the plot 300 can correspond to a time at which sustained flow of refrigerant is initiated (block 218). The period between time at the origin of the plot 300 and the time 304b can correspond to a first monitoring window 306 and a first portion of the treatment cycle during which pressure within the balloon 134 increases and then stabilizes toward a steady-state pressure. The period between the time 304b and the time 304c can correspond to a second monitoring window 308 and a second portion of the treatment cycle during which pressure within the balloon 134 is at least generally stable at the steady-state pressure. The time 304c can correspond to a time at which sustained flow of refrigerant is stopped (block 226). The period between the time 304c and the time 304d can correspond to a third monitoring window 310 and a third portion of the treatment cycle during which pressure within the balloon 134 decreases.

The inflation check (block 220) can include determining if a measured pressure at the time 304a is within a range characteristic of proper inflation of the balloon 134. The range, for example, can be between the pressure 302b, as a lower threshold of the range, and the pressure 302c, as an upper threshold of the range. The time 304a can be predetermined and selected to be during a sharp initial increase in pressure at the beginning of the first monitoring window 306. The upper and lower thresholds of the range can be determined empirically such that, at the time 304a, (a) if the measured pressure is below the lower threshold, it is indicative of a leak in the balloon 134, and (b) if the measured pressure is above the upper threshold, it is indicative of a blockage in the exhaust line 146 and/or a failure of a valve fluidically coupled to the exhaust line 146. In the illustrated embodiment, only one inflation check (block 220) is performed. In other embodiments, additional inflation checks (block 220) can be performed at different respective times during the first monitoring window 306.

The deflation check (block 228) can include determining if a measured pressure at the time 304d is below a threshold (e.g., the pressure 302a) indicating proper deflation of the balloon 134. The time 304d can be predetermined and selected to be during a gradual decrease in pressure within the cryotherapeutic element 122 and/or within the distal portion of the exhaust line 146 during the third monitoring window 310. The threshold can be determined empirically such that, at the time 304d, if the measured pressure is above the threshold, it is indicative of a blockage in the exhaust line 146 and/or a failure of a valve fluidically coupled to the exhaust line 146. In the illustrated embodiment, only one deflation check (block 228) is performed. In other embodiments, additional deflation checks (block 228) can be performed at different respective times during the third monitoring window 310.

The non-steady-state testing (block 222) and the steady-state testing (block 224) can correspond to the first and second monitoring windows 306, 308, respectively. During the first and second monitoring windows 306, 308, a rate of change in the measured pressure can be calculated and processed using first and second feedback loops, respectively. In both the first and second feedback loops, failure of the rate of change in the measured pressure to fall within a predetermined range between an upper threshold and a lower threshold can cause the flow of refrigerant through the supply line 140 to stop (block 230) and the system 100 to move to the error state (block 210). The first and second feedback loops can differ with respect to their upper thresholds, their lower thresholds, or both. For example, the range between the upper and lower thresholds of the first feedback loop can be wider than that for the second feedback loop since more change in the measured pressure is expected during the first monitoring window 306 than during the second monitoring window 308.

Processing the rate of change in the measured pressure within the balloon 134 and/or within the distal portion of the exhaust line 146 for conformity with a predetermined range may allow for significantly faster indications of at least some types of errors than would be possible by processing the measured pressure itself in the same manner. For example, if the balloon 134 were to rupture during a treatment cycle, the rate of change in the measured pressure would be affected almost immediately whereas it might take considerably longer for the measured pressure itself to fall to a level indicative of this type of error. Early detection of a rupture of the balloon 134 may allow the flow of refrigerant toward the balloon 134 to be stopped early enough to significantly reduce the possibility of leaked refrigerant causing a potentially harmful gas embolism.

Figure 4:
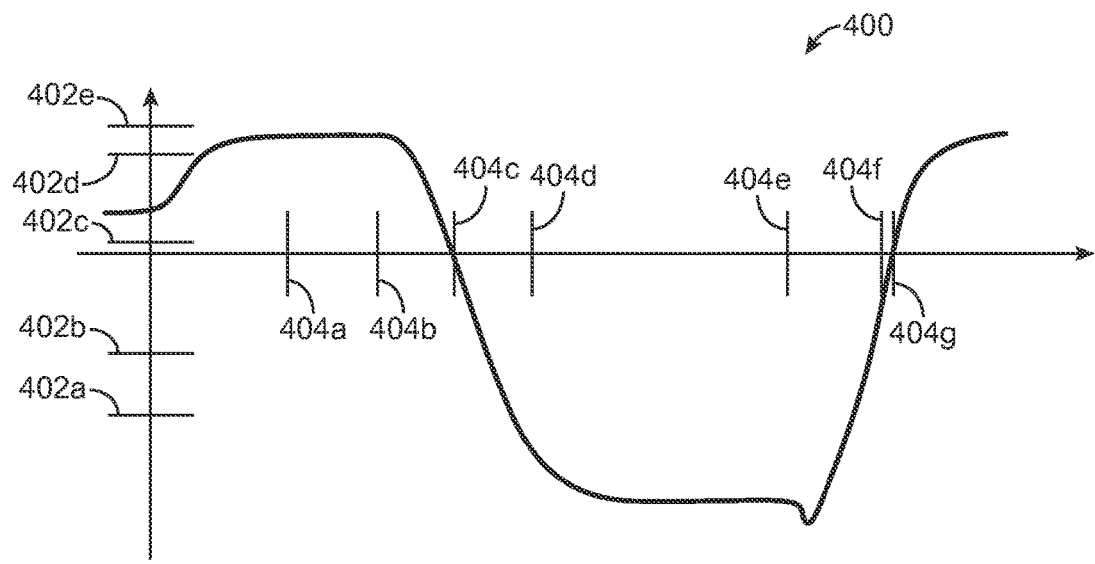
FIG. 4 is a plot of measured temperature (y-axis) relative to time (x-axis) during a neuromodulation procedure in accordance with an embodiment of the present technology.

FIG. 4 is a plot 400 of temperature (y-axis) within the cryotherapeutic element 122 and/or within the distal portion of the exhaust line 146 relative to time (x-axis) during a neuromodulation procedure in accordance with an embodiment of the present technology. With reference to FIGS. 2 and 4 together, along the y-axis of the plot 400 are a series of successively greater temperatures (individually identified as temperatures (402a-402e). Along the x-axis of the plot 400 are a series of successively greater times (individually identified as times 404a-404g). The times 404b, 404e can correspond, respectively, to a time at which sustained flow of refrigerant is initiated (block 218) and a time at which sustained flow of refrigerant is stopped (block 226).

Temperature can be used in addition to or instead of pressure as a basis for monitoring and controlling operation of the system 100. At the time 404a, an in-patient check can be performed to determine if the measured temperature is within a range between an upper threshold (e.g., the temperature 402e) and a lower threshold (e.g., the temperature 402d). Failure of the measured temperature to fall within this range can indicate that the cryotherapeutic element 122 is not positioned within a patient. At the time 404c, the measured temperature falling below a predetermined temperature threshold (e.g., 0° C.) can begin a timer for the treatment cycle. The time 404c may vary considerably between patients and between treatments on a single patient due, for example, to variability in factors such as anatomy, blood flow, positioning of the cryotherapeutic element 122, and delay in refrigerant delivery to the cryotherapeutic element 122. Accordingly, beginning the timer for the treatment cycle based on the predetermined temperature threshold may cause the actual time that tissue adjacent to the cryotherapeutic element 122 is exposed to cryotherapeutic temperatures to be more consistent than would be the case if the timer were initiated at a predetermined time. In at least some cases, a predetermined time is used as a back-up basis for beginning the timer. For example, beginning the timer based on the expiration of a predetermined time may override beginning the timer based on the predetermined temperature threshold. This can be useful, for example, to prevent the system 100 from stalling if the predetermined temperature threshold is not reached.

At time 404d, a cooling check can be performed. The cooling check can include determining if a measured temperature at the time 404d is below a threshold (e.g., the temperature 402a) indicating proper cooling of the balloon 134. The time 404d can be predetermined and selected to be during a gradual decrease in temperature within the cryotherapeutic element 122 and/or within the distal portion of the exhaust line 146. The threshold can be determined empirically such that, at the time 404d, if the measured temperature is above the threshold, it is indicative of an error within the system 100 that is causing the balloon 134 to cool unusually slowly. At time 404f, a warming check can be performed. The warming check can include determining if a measured temperature at the time 404f is above a threshold (e.g., the temperature 402b) indicating proper warming of the balloon 134. The time 404f can be predetermined and selected to be during a sharp increase in temperature within the cryotherapeutic element 122 and/or within the distal portion of the exhaust line 146. The threshold can be determined empirically such that, at the time 404f, if the measured temperature is below the threshold, it is indicative of an error within the system 100 that is causing the balloon 134 to warm unusually slowly. At the time 404g, if the measured temperature is above a predetermined threshold (e.g., the temperature 402c), the system 100 can indicate that the catheter 102 is safe to remove, such as because cryoadhesion is no longer present.

With reference to FIGS. 3 and 4 together, switching from the first monitoring window 306 to the second monitoring window 308 can be based on the measured pressure and/or the measured temperature. For example, switching from the first monitoring window 306 to the second monitoring window 308 can occur at the time 404c when the measured temperature is 0° C. Alternatively or in addition, switching from the first monitoring window 306 to the second monitoring window 308 can occur in response to a rate of change in the measured pressure stabilizing below a given threshold. Similar to beginning the timer for the treatment cycle based on the predetermined temperature threshold discussed above, switching from the first monitoring window 306 to the second monitoring window 308 based on the measured pressure and/or the measured temperature instead of a predetermined time can be useful to enhance consistency between treatments performed on the same or different patients. In at least some cases, a predetermined time is used as a back-up basis for switching from the first monitoring window 306 to the second monitoring window 308. For example, switching from the first monitoring window 306 to the second monitoring window 308 based on the expiration of a predetermined time may override switching from the first monitoring window 306 to the second monitoring window 308 based on the measured pressure and/or the measured temperature. This can be useful, for example, to prevent the system 100 from stalling if a predetermined threshold for the measured pressure and/or the measured temperature is not reached.

Figure 5:
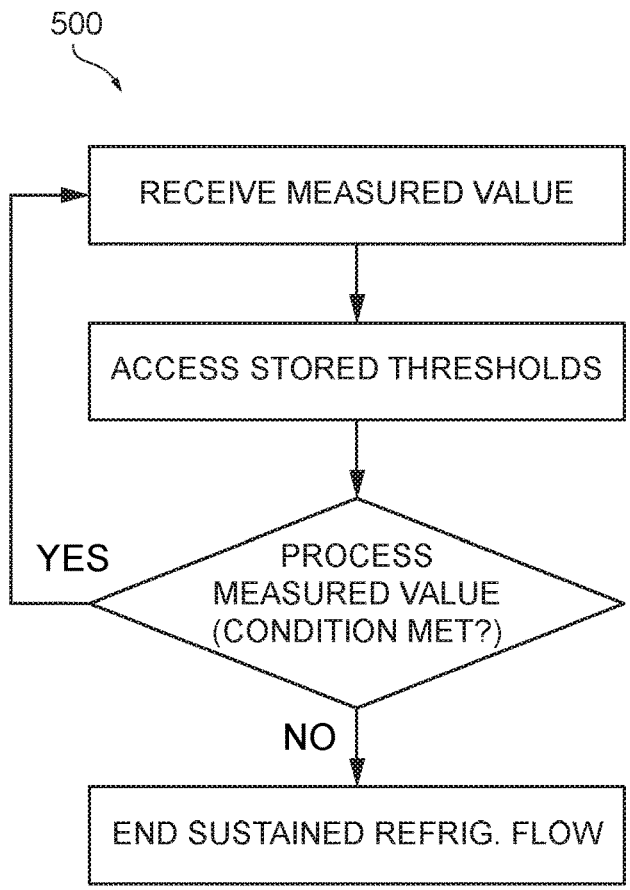
FIGS. 5 and 6 are flow charts illustrating, respectively, first and second algorithms within the method shown in FIG. 2.
Figure 6:
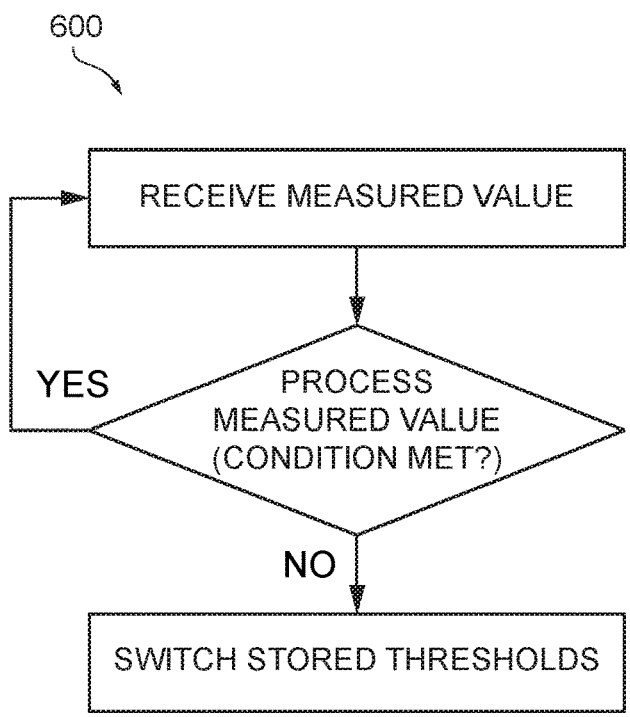

The control algorithm 130 (FIG. 1A) can include multiple parts (e.g., multiple code segments and/or subroutines) that are at least partially independent. For example, the control algorithm 130 can include a first algorithm (e.g., a checking algorithm) and a second algorithm (e.g., a switching algorithm) that cycle at different speeds. FIG. 5 a flow chart illustrating an example of a first algorithm 500. FIG. 6 a flow chart illustrating an example of the second algorithm 600. The first algorithm, for example, can execute the first and second feedback loops discussed above with reference to FIG. 3. The second algorithm, for example, can respond to an indication to switch from the first monitoring window 306 (FIG. 3) to the second monitoring window 308 (FIG. 3), such as by changing one or more stored values in a lookup table and thereby converting the first feedback loop into the second feedback loop. The first algorithm can access the stored values and compare them to a measured pressure received from the second pressure sensor 186 (FIG. 1A). Structuring the control algorithm 130 in this way may allow the first control algorithm to be operated at relatively high cycle speeds, such as cycle speeds greater than 1000 Hz. These cycle speeds, for example, can be at least 10 times faster than the cycle speeds at which the second algorithm operates. Alone or in addition to other features of the system 100, the relatively high cycle speeds of the first algorithm can enhance responsiveness to errors within the system 100 and thereby facilitate rapid mitigation of such errors.

Renal Neuromodulation

Catheters configured in accordance with at least some embodiments of the present technology can be well suited for performing renal neuromodulation in human patients. This can be the case, for example, with respect to the sizing, flexibility, operational characteristics, and/or other attributes of the catheters. Renal neuromodulation is the partial or complete incapacitation or other effective disruption of nerves of the kidneys, such as nerves terminating in the kidneys or in structures closely associated with the kidneys. In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Suitable anatomical locations for executing renal neuromodulation procedures include treatment location within or otherwise proximate to a renal lumen, such as a renal artery, a ureter, a renal pelvis, a major renal calyx, a minor renal calyx, or another suitable renal structure. In at least some cases, the treated tissue includes tissue at least proximate to a wall of a renal lumen. For example, with regard to a renal artery, a treatment procedure can include modulating nerves in the renal plexus, which lay intimately within or adjacent to the adventitia of the renal artery.

Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity and/or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Cryotherapeutic renal neuromodulation can include cooling tissue at a treatment location in a manner that modulates renal neural function. For example, sufficiently cooling at least a portion of a sympathetic renal nerve can slow or potentially block conduction of neural signals along the nerve to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a vessel or chamber wall such that tissue is effectively cooled to a depth where sympathetic renal nerves reside. For example, in some embodiments, a cryotherapeutic element is cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

ADDITIONAL EXAMPLES

1. A method, comprising:
    advancing an elongate shaft of a catheter toward a treatment location within a body lumen of a human patient;
    directing a flow of refrigerant toward a cryotherapeutic element at a distal end portion of the shaft via a supply line extending along at least a portion of a length of the shaft;

expanding the directed refrigerant to cause cooling within a balloon of the cryotherapeutic element;
exhausting the expanded refrigerant via an exhaust line extending along at least a portion of the length of the shaft;
measuring pressure within the cryotherapeutic element and/or within a distal portion of the exhaust line via a monitoring line extending along at least a portion of the length of the shaft;
calculating a rate of change of the measured pressure;
processing the rate of change of the measured pressure using a first feedback loop during a first monitoring window of a treatment cycle, the first feedback loop being configured to cause the flow of refrigerant through the supply line to stop if the rate of change of the measured pressure falls outside a range from a first lower threshold to a first upper threshold;
switching from the first monitoring window to a second monitoring window of the treatment cycle; and
processing the rate of change of the measured pressure using a second feedback loop during the second monitoring window, the second feedback loop being configured to cause the flow of refrigerant through the supply line to stop if the rate of change of the measured pressure falls outside a range from a second lower threshold to a second upper threshold,
wherein (a) the first lower threshold is different than the second lower threshold, (b) the first upper threshold is different than the second upper threshold, or (c) both (a) and (b).

2. The method of example 1 wherein:
the first monitoring window corresponds to a first portion of the treatment cycle, the first portion of the treatment cycle being characterized by pressure within the balloon increasing and then stabilizing toward a steady-state pressure; and
the second monitoring window corresponds to a second portion of the treatment cycle, the second portion of the treatment cycle being characterized by pressure within the balloon remaining at least generally at the steady-state pressure.

3. The method of any of the preceding examples, further comprising:
starting the flow of refrigerant through the supply line;
measuring a pressure within the cryotherapeutic element and/or within the distal portion of the exhaust line via the monitoring line upon expiration of a predetermined time period immediately following starting the flow of refrigerant; and
performing an inflation check including determining if the measured pressure is within a range characteristic of proper inflation of the balloon.

4. The method of any of the preceding examples, further comprising:
stopping the flow of refrigerant through the supply line;
measuring a pressure within the cryotherapeutic element and/or within the distal portion of the exhaust line via the monitoring line upon expiration of a predetermined time period following stopping the flow of refrigerant; and
performing a deflation check including determining if the measured pressure is below a threshold indicating proper deflation of the balloon.

5. The method of any of examples 1, 2 and 4, further comprising:
starting the flow of refrigerant through the supply line;
measuring a temperature within the cryotherapeutic element and/or within the distal portion of the exhaust line via a sensor lead extending along at least a portion of the length of the shaft upon expiration of a predetermined time period after starting the flow of refrigerant; and
performing a cooling check including determining if the measured temperature is below a threshold indicating proper cooling of the balloon.

6. The method of any of examples 1-3 and 5, further comprising:
stopping the flow of refrigerant through the supply line;
measuring a temperature within the cryotherapeutic element and/or within the distal portion of the exhaust line via a sensor lead extending along at least a portion of the length of the shaft upon expiration of a predetermined time period after stopping the flow of refrigerant; and
performing a warming check including determining if the measured temperature is above a threshold indicating proper warming of the balloon.

7. The method of any of examples 1-4, further comprising measuring temperature within the cryotherapeutic element and/or within the distal portion of the exhaust line via a sensor lead extending along at least a portion of the length of the shaft, wherein switching from the first monitoring window to the second monitoring window includes switching from the first monitoring window to the second monitoring window based at least partially on the measured temperature.

8. The method of any of examples 1, 2 and 5-7 wherein switching from the first monitoring window to the second monitoring window includes switching from the first monitoring window to the second monitoring window based at least partially on the measured pressure.

9. The method of any of the preceding examples, further comprising:
releasing a pulse of refrigerant into the balloon via the supply line;
measuring a pressure within the exhaust line after releasing the pulse; and
performing a pre-inflation check including determining if the measured pressure within the exhaust line is within a range indicating that the balloon is intact.

10. The method of example 9 wherein:
releasing the pulse includes releasing a first pulse; and
the method further comprises:
releasing a second pulse of refrigerant into the balloon via the supply line after performing the pre-inflation check,
measuring a pressure within the balloon and/or within a distal portion of the exhaust line after releasing the second pulse, and
performing a pressure-decay test including determining if the measured pressure within the balloon and/or within a distal portion of the exhaust line is within a range indicating that the balloon is intact.

11. The method of any of examples 1-4 and 8-10, further comprising measuring temperature within the cryotherapeutic element and/or within the distal portion of the exhaust line via a sensor lead extending along at least a portion of the length of the shaft, wherein switching from the first monitoring window to the second monitoring window includes switching from the first monitoring window to the second monitoring window based at least partially on a predetermined time, the measured temperature, the measured pressure, or a combination thereof.

12. The method of example 11 wherein switching from the first monitoring window to the second monitoring window includes switching from the first monitoring window to the second monitoring window using a switching algorithm in which switching based on the measured temperature, the measured pressure, or a combination thereof can only occur prior to expiration of the predetermined time.

13. The method of any of the preceding examples wherein:
measuring pressure and processing the measured pressure using the first feedback loop are executed by a first control algorithm operating at a first cycle speed;
switching from the first monitoring window to the second monitoring window is executed by a second control algorithm operating at a second cycle speed; and
the first cycle speed is faster than the second cycle speed.

14. The method of example 13 wherein the first cycle speed is at least 10 times faster than the second cycle speed.

15. The method of example 12 or 13 wherein:
processing the rate of change of the measured pressure using the first feedback loop includes, within the first control algorithm, accessing a first stored value as the first lower threshold and accessing a second stored value as the first upper threshold; and
switching from the first monitoring window to the second monitoring window includes converting the first feedback loop into the second feedback loop by, within the second control algorithm, (a) changing the first stored value from the first lower threshold to the second lower threshold, (b) changing the second stored value from the first upper threshold to the second upper threshold, or (c) both (a) and (b).

16. The method of any of the preceding examples, further comprising priming refrigerant downstream from the refrigerant supply so as to increase a liquid fraction of the refrigerant, wherein directing the refrigerant includes opening a fluidic connection between the refrigerant supply and the supply line after priming the refrigerant.

17. The method of example 16 wherein priming the refrigerant includes bleeding the refrigerant from a valve downstream from the refrigerant supply.

18. A method including any non-conflicting combination of examples 1-17.

19. An apparatus configured to perform any of the methods of examples 1-18.

20. A method, comprising:
advancing an elongate shaft of a catheter toward a treatment location within a body lumen of a human patient;
pre-inflating the balloon after advancing the shaft;
performing a pressure-decay test on the pre-inflated balloon;
priming a refrigerant supply after performing the pressure-decay test, wherein priming the refrigerant supply includes increasing a liquid fraction of refrigerant flowing from the refrigerant supply toward a supply line extending along at least a portion of a length of the shaft;
starting a flow of refrigerant toward a cryotherapeutic element at a distal end portion of the shaft via the supply line after priming the refrigerant supply;
expanding the refrigerant causing cooling within a balloon of the cryotherapeutic element;
exhausting the expanded refrigerant via an exhaust line extending along at least a portion of the length of the shaft;
measuring a first pressure within the cryotherapeutic element and/or within a distal portion of the exhaust line via a monitoring line extending along at least a portion of the length of the shaft after a predetermined time period immediately following starting the flow of refrigerant;
performing an inflation check including determining if the measured first pressure is within a desired inflation range;
stopping the flow of refrigerant through the supply line;
measuring a second pressure within the cryotherapeutic element and/or within the distal portion of the exhaust line via the monitoring line after a predetermined time period immediately following stopping the flow of refrigerant; and
performing a deflation check including determining if the measured second pressure is within a desired deflation range.

21. The method of example 20, further comprising:
measuring a temperature within the cryotherapeutic element and/or within the distal portion of the exhaust line via a sensor lead extending along at least a portion of the length of the shaft upon expiration of a predetermined time period after starting the flow of refrigerant; and
performing a cooling check including determining if the measured temperature is within a desired cooling range.

22. The method of example 21 wherein measuring the temperature includes measuring a first temperature, and the method further comprises:
measuring a second temperature within the cryotherapeutic element and/or within the distal portion of the exhaust line via the sensor lead upon expiration of a predetermined time period after stopping the flow of refrigerant; and
performing a warming check including determining if the measured second temperature is within a desired warming range.

23. An apparatus configured to perform any of the methods of examples 20-22.

24. A method, comprising:
advancing an elongate shaft of a catheter toward a treatment location within a body lumen of a human patient;
directing a flow of refrigerant toward a cryotherapeutic element at a distal end portion of the shaft via a supply line extending along at least a portion of a length of the shaft;
expanding the directed refrigerant to cause cooling within a balloon of the cryotherapeutic element;
exhausting the expanded refrigerant via an exhaust line extending along at least a portion of the length of the shaft;
measuring pressure within the cryotherapeutic element and/or within a distal portion of the exhaust line via a monitoring line extending along at least a portion of the length of the shaft;
calculating a rate of change of the measured pressure; and
processing the calculated rate of change using a feedback loop configured to cause the flow of refrigerant through the supply line to stop if the calculated rate of change falls outside a range from a lower threshold to an upper threshold.

25. The method of example 24 wherein:
the balloon is a single-walled balloon; and
expanding the directed refrigerant causes the balloon to increase in volume and press against a wall of the body lumen with an outer surface of the balloon in direct contact with an inner surface of the wall of the body lumen and an inner surface of the balloon in direct contact with the expanded refrigerant.

26. The method of example 24 or 25, further comprising:
measuring a pressure within the cryotherapeutic element and/or within the distal portion of the exhaust line via the monitoring line upon expiration of a predetermined time period after beginning the flow of refrigerant through the supply line; and
performing an inflation check including determining if the measured pressure is within a range characteristic of proper inflation of the balloon.

27. An apparatus configured to perform any of the methods of examples 24-26.

28. A system, comprising:
a catheter including—
an elongate shaft,
a cryotherapeutic element operably connected to the shaft, the cryotherapeutic element including a balloon,
an exhaust line operably connected to the cryotherapeutic element and extending along at least a portion of a length of the shaft,
a supply line operably connected to the cryotherapeutic element and extending along at least a portion of the length of the shaft, and
a monitoring line extending along at least a portion of the length of the shaft; a controller including—
processing circuitry; and
memory storing instructions that, when executed, cause the processing circuitry to perform a method comprising—
measuring pressure within the cryotherapeutic element and/or within a distal portion of the exhaust line via the monitoring line;
calculating a rate of change of the measured pressure;
processing the rate of change using a first feedback loop during a first monitoring window of a treatment cycle, the first feedback loop being configured to cause a flow of refrigerant through the supply line to stop if the rate of change of the measured pressure falls outside a range from a first lower threshold to a first upper threshold;
switching from the first monitoring window to a second monitoring window of the treatment cycle; and
processing the rate of change of the measured pressure using a second feedback loop during the second monitoring window, the second feedback loop being configured to cause the flow of refrigerant through the supply line to stop if the rate of change of the measured pressure falls outside a range from a second lower threshold to a second upper threshold,
wherein (a) the first lower threshold is different than the second lower threshold, (b) the first upper threshold is different than the second upper threshold, or (c) both (a) and (b).

29. The system of example 28 wherein the balloon is a single-walled balloon.

30. The system of example 28 or 29, further comprising a sensor lead extending along at least a portion of the length of the shaft, wherein:
the method includes measuring temperature within the cryotherapeutic element and/or within the distal portion of the exhaust line via the sensor lead, and
switching from the first monitoring window to the second monitoring window includes switching from the first monitoring window to the second monitoring window based at least partially on the measured temperature, the measured pressure, or a combination thereof.

31. A computer-readable medium storing computer-executable instructions that, when executed, cause a computer system to perform a method of controlling a cryotherapeutic system, the method comprising:
receiving a pressure reading from a pressure sensor of the cryotherapeutic system;
calculating a rate of change of the pressure reading;
processing the rate of change using a first feedback loop during a first monitoring window of a treatment cycle;
if the rate of change falls outside a range from a first lower threshold to a first upper threshold of the first feedback loop during the first monitoring window, instructing the cryotherapeutic system to stop a flow of refrigerant through a supply line of the cryotherapeutic system;
switching from the first monitoring window to a second monitoring window of the treatment cycle;
processing the rate of change using a second feedback loop during the second monitoring window; and
if the rate of change falls outside a range from a second lower threshold to a second upper threshold of the second feedback loop during the second monitoring window, instructing the cryotherapeutic system to stop the flow of refrigerant through the supply line,
wherein (a) the first lower threshold is different than the second lower threshold, (b) the first upper threshold is different than the second upper threshold, or (c) both (a) and (b).

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments may also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

The methods disclosed herein include and encompass, in addition to methods of practicing the present technology (e.g., methods of making and using the disclosed devices and systems), methods of instructing others to practice the present technology. For example, a method in accordance with a particular embodiment includes advancing an elongate shaft toward a treatment location within a body lumen, pre-inflating a balloon, performing a pressure-decay test, priming a refrigerant supply, starting a flow of refrigerant, expanding the refrigerant, exhausting the expanded refrigerant, measuring a pressure within the balloon, performing an inflation check, stopping the flow of refrigerant, and performing a deflation check. A method in accordance with another embodiment includes instructing such a method.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments of the present technology.

We claim:

1. A method, comprising:
 advancing an elongate shaft of a catheter toward a treatment location within a body lumen of a human patient;
 directing a flow of refrigerant toward a cryotherapeutic element at a distal end portion of the shaft via a supply line extending along at least a portion of a length of the shaft;
 expanding the directed refrigerant to cause cooling within a balloon of the cryotherapeutic element;
 exhausting the expanded refrigerant via an exhaust line extending along at least a portion of the length of the shaft;
 measuring pressure within the cryotherapeutic element and/or within a distal portion of the exhaust line via a monitoring line extending along at least a portion of the length of the shaft;
 calculating a rate of change of the measured pressure;
 processing the rate of change of the measured pressure using a first feedback loop during a first monitoring window of a treatment cycle, the first feedback loop being configured to cause the flow of refrigerant through the supply line to stop if the rate of change of the measured pressure falls outside a range from a first lower threshold to a first upper threshold;
 switching from the first monitoring window to a second monitoring window of the treatment cycle; and
 processing the rate of change of the measured pressure using a second feedback loop during the second monitoring window, the second feedback loop being configured to cause the flow of refrigerant through the supply line to stop if the rate of change of the measured pressure falls outside a range from a second lower threshold to a second upper threshold, wherein (a) the first lower threshold is different than the second lower threshold and/or (b) the first upper threshold is different than the second upper threshold.

2. The method of claim 1, wherein:
 the first monitoring window corresponds to a first portion of the treatment cycle, the first portion of the treatment cycle being characterized by pressure within the balloon increasing and then stabilizing toward a steady-state pressure; and
 the second monitoring window corresponds to a second portion of the treatment cycle, the second portion of the treatment cycle being characterized by pressure within the balloon remaining at least generally at the steady-state pressure.

3. The method of claim 1, further comprising:
 starting the flow of refrigerant through the supply line;
 measuring a pressure within the cryotherapeutic element and/or within the distal portion of the exhaust line via the monitoring line upon expiration of a predetermined time period immediately following starting the flow of refrigerant; and
 performing an inflation check including determining if the measured pressure is within a range characteristic of proper inflation of the balloon.

4. The method of claim 1, further comprising:
 stopping the flow of refrigerant through the supply line;
 measuring a pressure within the cryotherapeutic element and/or within the distal portion of the exhaust line via the monitoring line upon expiration of a predetermined time period following stopping the flow of refrigerant; and
 performing a deflation check including determining if the measured pressure is below a threshold indicating proper deflation of the balloon.

5. The method of claim 1, further comprising:
 starting the flow of refrigerant through the supply line;
 measuring a temperature within the cryotherapeutic element and/or within the distal portion of the exhaust line via a sensor lead extending along at least a portion of the length of the shaft upon expiration of a predetermined time period after starting the flow of refrigerant; and
 performing a cooling check including determining if the measured temperature is below a threshold indicating proper cooling of the balloon.

6. The method of claim 1, further comprising:
 stopping the flow of refrigerant through the supply line;
 measuring a temperature within the cryotherapeutic element and/or within the distal portion of the exhaust line via a sensor lead extending along at least a portion of the length of the shaft upon expiration of a predetermined time period after stopping the flow of refrigerant; and performing a warming check including determining if the measured temperature is above a threshold indicating proper warming of the balloon.

7. The method of claim 1, further comprising measuring a temperature within the cryotherapeutic element and/or within the distal portion of the exhaust line via a sensor lead extending along at least a portion of the length of the shaft, wherein switching from the first monitoring window to the second monitoring window includes switching from the first monitoring window to the second monitoring window based at least partially on the measured temperature.

8. The method of claim 1, wherein switching from the first monitoring window to the second monitoring window includes switching from the first monitoring window to the second monitoring window based at least partially on the measured pressure.

9. The method of claim 1, further comprising:
releasing a pulse of refrigerant into the balloon via the supply line;
measuring a pressure within the exhaust line after releasing the pulse; and
performing a pre-inflation check including determining if the measured pressure within the exhaust line is within a range indicating that the balloon is intact.

10. The method of claim 9, wherein:
releasing the pulse includes releasing a first pulse; and
the method further comprises:
releasing a second pulse of refrigerant into the balloon via the supply line after performing the pre-inflation check,
measuring a pressure within the balloon and/or within a distal portion of the exhaust line after releasing the second pulse, and
performing a pressure-decay test including determining if the measured pressure within the balloon and/or within a distal portion of the exhaust line is within a range indicating that the balloon is intact.

11. The method of claim 1, further comprising measuring a temperature within the cryotherapeutic element and/or within the distal portion of the exhaust line via a sensor lead extending along at least a portion of the length of the shaft, wherein switching from the first monitoring window to the second monitoring window includes switching from the first monitoring window to the second monitoring window based at least partially on a predetermined time, the measured temperature, the measured pressure, or a combination thereof.

12. The method of claim 11, wherein switching from the first monitoring window to the second monitoring window includes switching from the first monitoring window to the second monitoring window using a switching algorithm in which switching based on the measured temperature, the measured pressure, or a combination thereof can only occur prior to expiration of the predetermined time.

13. The method of claim 1, wherein:
measuring pressure and processing the measured pressure using the first feedback loop are executed by a first control algorithm operating at a first cycle speed;
switching from the first monitoring window to the second monitoring window is executed by a second control algorithm operating at a second cycle speed; and
the first cycle speed is faster than the second cycle speed.

14. The method of claim 13, wherein the first cycle speed is at least 10 times faster than the second cycle speed.

15. The method of claim 13, wherein:
processing the rate of change of the measured pressure using the first feedback loop includes, within the first control algorithm, accessing a first stored value as the first lower threshold and accessing a second stored value as the first upper threshold; and
switching from the first monitoring window to the second monitoring window includes converting the first feedback loop into the second feedback loop by, within the second control algorithm, (a) changing the first stored value from the first lower threshold to the second lower threshold and/or (b) changing the second stored value from the first upper threshold to the second upper threshold.

* * * * *